(12) United States Patent
Marsh et al.

(10) Patent No.: US 6,268,607 B1
(45) Date of Patent: Jul. 31, 2001

(54) UV PURIFICATION OF AIR AND WATER IN DENTAL OPERATORIES

(75) Inventors: Leonard Marsh, Hackensack, NJ (US); Michael Radicone, Oceanside, NY (US); Richard W. Hanson, Beaverton, OR (US)

(73) Assignee: DCI International, Inc., Newberg, OR (US)

( * ) Notice: Subject to any disclaimer, the term of this patent is extended or adjusted under 35 U.S.C. 154(b) by 0 days.

(21) Appl. No.: 09/199,593

(22) Filed: Nov. 25, 1998

Related U.S. Application Data
(60) Provisional application No. 60/066,628, filed on Nov. 26, 1997.

(51) Int. Cl.[7] .................................................... C02F 1/48
(52) U.S. Cl. .............................. 250/455.11; 250/454.11; 250/504 R; 210/232; 422/186.3
(58) Field of Search .......................... 250/455.11, 454.11, 250/432 R, 504 R; 210/205, 209, 232, 435, 443; 422/186.3

(56) References Cited

U.S. PATENT DOCUMENTS

| Re. 34,513 | * | 1/1994 | Ellner | 350/432 R |
|---|---|---|---|---|
| 5,573,666 | * | 11/1996 | Korin | 210/232 |
| 5,935,431 | * | 8/1999 | Korin | 210/205 |
| 6,139,726 | * | 10/2000 | Greene | 210/94 |

* cited by examiner

Primary Examiner—Kiet T. Nguyen
(74) Attorney, Agent, or Firm—TraskBritt, P.C.

(57) ABSTRACT

A dental office is provided with a system to purify air and/or water delivered to the operatory. Purification is by UV-C light applied to the utilities as they are transported from supply to delivery sites. Ideally, the system includes separate devices structured and arranged to effect purification of the ambient air circulating within the operatory; the water supplied to the operatory and the water delivered to and through dental hand pieces in connection with a procedure.

22 Claims, 1 Drawing Sheet

UV PURIFICATION OF AIR AND WATER IN DENTAL OPERATORIES

PRIORITY

This application claims the priority of U.S. Provisional Patent Application Ser. No. 60/066,628 filed Nov. 26, 1997.

BACKGROUND OF THE INVENTION

1. Field

This invention relates to the use of UV light for the purification of air and water. It is particularly directed to apparatus and methodology specifically useful in clinical surroundings, notably dental operatories.

2. State of the Art

Ultraviolet (UV) radiation has been widely investigated for its potential utility in air and water purification applications. The portion of the electromagnetic spectrum having wave lengths between about 1000 and about 4000 Å (angstrom units) is conventionally referred to as "ultraviolet light," even though it is not visible to the human eye. An angstrom unit is one ten billionth of a meter. The UV spectrum is alternatively defined as comprising wavelengths between about 100 and about 400 nm (nanometers). The UV portion of the spectrum is further arbitrarily divided into three band widths; specifically: UV-A (long-wave, above 320 nm), UV-B (medium wave, between about 280 and about 320 nm) and UV-C (short-wave, between about 100 and about 280 nm). UV-C radiation has been found to possess the greatest germicidal effectiveness, a wave length of 253.7 nm being commonly referred to as "germicidal UV."

UV-C radiation has been used commercially for air purification. U.S. Pat. No. 4,422,824, for example, discloses a ceiling fan with blades housing germicidal (UV) light bulbs. The blades are structured with chambers to direct air past the lights, thereby exposing airborne micro-organisms to UV light.

The germicidal effectiveness of UV-C radiation against both air-borne and water-borne microorganisms is discussed in the article "Ultraviolet Water Purification," *Pollution Engineering Magazine*, Vol. 5, No. 12, December, 1973. This article, the disclosure of which is incorporated by reference as a portion of this specification, describes practical constructions of germicidal lamps and water purification systems utilizing such lamps. Modem UV water treatment systems are disclosed by U.S. Pat. Nos. 5,401,394 and 5,536,395. The article, "Applications for Ultraviolet," Ann M. Wysocki, *Water Conditioning and Purification Magazine*, May 1988, describes a water purifier and proposes a number of practical applications for such a device. This article, which is incorporated by reference as a part of this specification, also details a set of criteria for an acceptable ultraviolet disinfecting unit.

One important consideration in the utilization of UV radiation in a space normally occupied by humans, is the safe exposure limit to such radiation. The National Institute for Occupational Safety and Health (NIOSH) has adopted as "safe" an exposure below the level found to cause eye irritation. In the case of germicidal UV (253.7 nm), the safe exposure limit is less than $0.2\ \mu watt/cm^2$ over any eight-hour period.

UV light has apparently not found practical application in dental operatories for air and water purification. U.S. Pat. No. 5,204,004 discloses a water line filtration system for dental operatories. The system is designed to prevent water flowing through a supply line to a hand piece from carrying bacterial contamination into a patient's mouth. The biofilm which normally forms in such a supply line is identified as a source of bacterial contamination for dental patients. U.S. Pat. No. 5,556,279 discloses a water purification system for dental instruments. The system is typical of equipment found in dental operatories, and consists of a disposable cartridge element comprising activated carbon and exchange resins disposed in a water supply line.

BRIEF SUMMARY OF THE INVENTION

A dental office is provided with a system to purify air and/or water delivered to the operatory. Purification is by means of UV-C light applied to the utilities as they are transported from supply to delivery sites. Ideally, the system includes separate devices structured and arranged to effect purification of the ambient air circulating within the operatory, the water supplied to the operatory and the water delivered to and through dental hand pieces in connection with a procedure.

The devices relied upon for ambient air and normal utility water purification may be patterned after conventional UV systems, but sized and configured appropriately to assure adequate biocidal activity within the safe exposure limit for humans. A special purpose device is provided for the purification of water delivered through a dental delivery system. This device comprises a simple in line purifier and requires no special controls, valves or plumbing.

As presently contemplated, this invention may be embodied as a water purification system for a dental operatory. The system may be supported by a mounting bracket suspended from the support structure of a dental delivery system. Mounting structure associated with the mounting bracket will generally include reservoir support structure, germicidal bulb support structure, and quartz tube support structure. A water reservoir is typically suspended from the reservoir support structure in fluid-tight association with that structure. A germicidal UV bulb will be suspended from the germicidal bulb support structure, approximately coaxially with the reservoir, which is typically, but not necessarily, shaped as a cylinder with a circular cross section. The bulb will in most cases have a first end proximate the support structure and a second end remote from the support structure. A quartz tube may be held by the quartz tube support structure, approximately coaxially with the germicidal UV bulb. An inlet, usually associated with the support structure, is structured and arranged to deliver water to the interior of the reservoir near the second end of the bulb. An outlet, also usually associated with the support structure, is structured and arranged to receive water from the interior of the reservoir from a location near the first end of the bulb.

In general, the in line purifier of this invention may conveniently be constructed and arranged for mounting to a dental support post of the kind conventionally present in a dental operatory. Alternatively, the purifier may be mounted from a wall or a frame structure in the proximity of a dental delivery unit. In any case, the purifier is generally suspended from a mounting bracket structured as required to interface with the support structure selected for a specific installation. A reservoir, such as a tank, is suspended from the post or other support structure, usually in approximately parallel orientation, and contains a supply of water as well as the germicidal components of the system. An inlet provides water to the reservoir, ideally near its bottom. Water is displaced upwardly through the reservoir, eventually exiting through an outlet at its top. The volume of the reservoir is selected to assure a specified minimum dwell time of water in the reservoir as it flows through the system under peak use conditions. The dwell time should be sufficient to permit a germicidally effective exposure to UV light of the water during peak use conditions. A reservoir volume of about 10 to about 40 cubic inches constitutes the operable range for most dental applications, with volumes between about 15 and about 35 cubic inches constituting the preferred practical range, based upon the usual water volume requirements of such operatories.

UV light may be provided by means of an elongate germicidal UV bulb suspended within a quartz tube mounted approximately coaxially with the bulb and the reservoir. The annular volume thereby formed between the quartz tube and the interior wall surface of the reservoir functions as a treatment zone. Water is introduced to the bottom of this zone, assuring that it travels the full length of the UV bulb to reach the outlet at the top of the zone. In this fashion, maximum UV exposure of the water is assured.

The reservoir tank and quartz tube require periodic cleaning. They are thus preferably associated through structural means which permit removal of these components without disconnecting water lines at the inlet and outlet. Ideally, the quartz tube is removable without otherwise disturbing the mounted status of the assembly. It is highly preferred to organize and mount the assembly such that the quartz tube and bulb can be removed while leaving the reservoir filled with water.

The assembly may be enclosed with an aesthetically pleasing cover. A portion of this covering may be provided with a window so that an observer can see whether the UV bulb is functioning. According to the preferred embodiments of the invention, all of the components previously described as being suspended from a mounting post or other support structure are mounted internally of other components of the dental delivery system or cart typically present in an operatory.

In summary, the invention may be regarded as a water purification system for a dental operatory. The system comprises a mounting bracket suspended from support structure of a dental delivery system; mounting structure associated with that mounting bracket, including reservoir support structure, germicidal bulb support structure, and quartz tube support structure; a water reservoir suspended from the reservoir support structure in fluid-tight association therewith; a germicidal UV bulb suspended from the germicidal bulb support structure, approximately coaxially with the reservoir, the bulb having a first end proximate the support structure and a second end remote from the support structure; a quartz tube held by the quartz tube support structure, approximately coaxially with the germicidal UV bulb; an inlet, structured and arranged to deliver water to the interior of the reservoir near the second end of the bulb; and an outlet, structured and arranged to receive water from the interior of the reservoir from a location near the first end of the bulb. The quartz tube support structure may be constructed and arranged to permit removal of the quartz tube while water lines are connected to the inlet and the outlet. The system may be structured and arranged to permit removal of the quartz tube while the UV bulb, bulb support structure and reservoir support structure remain in position. It may further be structured and arranged such that the quartz tube may be removed without moving the reservoir in a manner tending to spill water from the reservoir, ideally while the reservoir is full of water. The capacity of the reservoir is ideally selected to assure a germicidally effective dwell time of water within the reservoir while water is being withdrawn from the reservoir at a flow rate required by the dental operatory. In most practical embodiments, the capacity of the reservoir is between approximately 16 and approximately 35 cubic inches. The system may also be structured and arranged to direct water entering the reservoir to a selected region of the interior of the reservoir, whereby to maximize the exposure of fresh water to UV light. Water entering the reservoir is generally directed to a lower portion of the reservoir, most often to the perimeter of the interior of the reservoir. It is useful for the system to include an indicator of the operational status of the bulb. The indicator should be visible from a wide view angle within the operatory. A strategically placed UV-light-reactive surface within the reservoir enhances the visibility of the indicator. Such a surface may be inherently provided by the interior surface of the reservoir when it is constructed of stainless steel. Preferred embodiments of the water purification system of this invention are structured and arranged to permit removal of the bulb without tools and without removing the reservoir or the quartz tube from their respective support structures. Preferably means are included for heating water within the reservoir to above room temperature, as are control means for maintaining the temperature of water within the reservoir to below a selected temperature above approximately human body temperature, ideally approximately 105° F. The system may also include limit means constructed and arranged to prevent the temperature of the reservoir from exceeding the selected temperature, even though the reservoir contains no water.

BRIEF DESCRIPTION OF THE SEVERAL VIEWS OF THE DRAWING

In the drawings, which illustrate what is currently regarded as the best mode for carrying out the invention.

DETAILED DESCRIPTION OF THE INVENTION

Figures 2, 3:
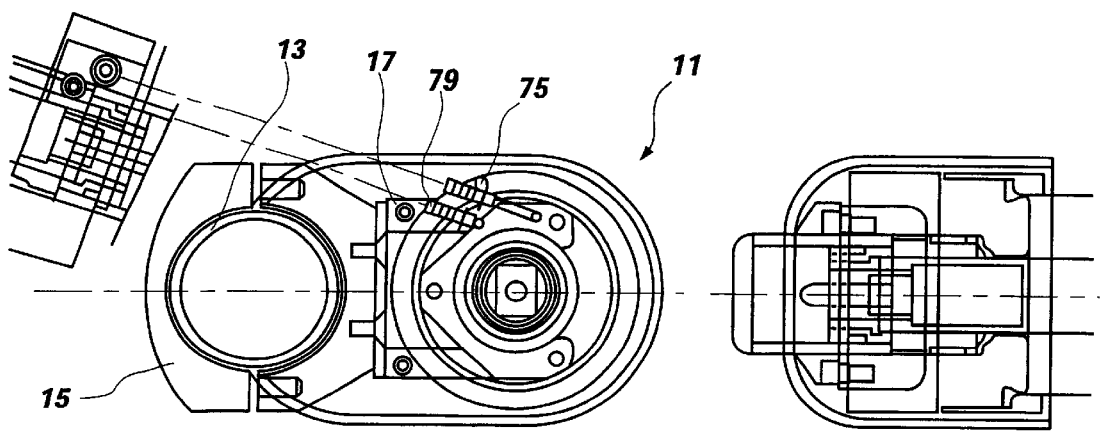
FIG. 2 is a top view of the apparatus of FIG. 1.
FIG. 3 is a fragmentary view of the apparatus of FIG. 2, rotated 90° counterclockwise with respect to FIGS. 1 and 2.
Figure 1:
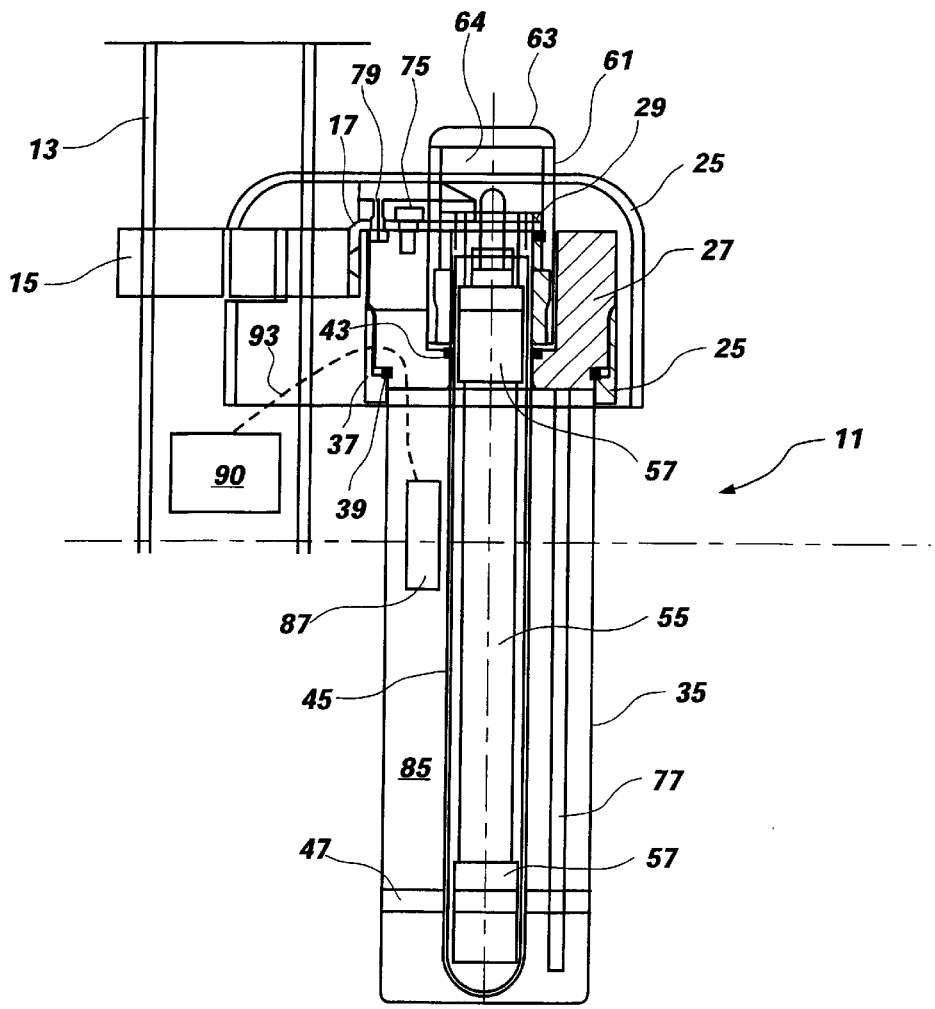
FIG. 1 is a cross-sectional view in side elevation of a UV water purification assembly of this invention mounted to a support.

Water-purification assembly, generally 11, is attached to a support post 13 by means of a clamp 15 and bracket 17 support system. The assembly 11 is held to the bracket 17 by means of a clamp ring 25, an outer gland 27 and an inner gland 29. As illustrated, a stainless steel drawn tank 35 is suspended from the clamp ring 25 by an outward lip 37. The ring 25 is threaded upon the gland 27 to squeeze an o-ring 39, thereby effecting a fluid-tight seal. This arrangement facilitates the periodic removal of the tank 35 for cleaning.

The inner gland 29 threads into the outer gland 27 as shown to compress an o-ring 43 to effect a second fluid-tight seal at the joint of a quartz tube 45. This tube 45 is suspended directly from the inner gland 29, and is held in position within the tank 35 by a centering guide 47. It is removable from the assembly for periodic cleaning or replacement by simply rotating the gland 29 to loosen pressure against the o-ring 43.

A germicidal UV bulb 55 is suspended from the bracket 17 within the quartz tube 45. Bushings 57, at each end of the bulb 55, hold the bulb in proper position within the tube 45. An indicator housing 61, with a transparent upper window 63 slips over the gland 29 and provides means for an operator to observe the "on" or "off" status of the bulb 55. Window 63 therefore may serve as one embodiment of a status indicator for bulb 55. A UV ight reactive surface, such as indicated at interior surface 64, may additionally be used further to enhance visibility of the bulb status indicator 63. An aesthetic cover 65 encloses the mounting components of the assembly.

An inlet port 75 receives water from a utility line (not shown), and directs it through an inlet tube 77 to the bottom portion of the tank 35, below the centering guide 47. Water rises up through the tank, being drawn out through an outlet port 79 through supply tubing (not shown) associated with hand pieces, notably water cooled drills or syringes, of a dental delivery system mounted to the post 13.

The illustrated arrangement provides purified water on an as-needed basis through an unobtrusive, safe assembly. UV radiation is effectively contained within the tank 35 and water-filled annular treatment zone 85. The temperature of water contained in zone 85 may be adjusted by temperature regulator device 87 and temperature controller 90. A waterproof temperature control means, typically including a feedback signal, is indicated by dashed line 93 between the controller 90 and the regulating device 87. Temperature of the water may be maintained at a desired level by setting the controller 90. A desired water temperature setting may be above room temperature, including above approximately human body temperature. One particularly desirable water temperature is approximately 105 degrees Fahrenheit. The controller 90 and control means 93 desirably cooperate to limit the temperature of the reservoir even in the case where the reservoir contains no water. In the case where bulb 55 is the temperature regulator device, the temperature of bulb 55 functions to automatically limit water temperature without need for controller 90.

Reference herein to details of the preferred embodiment is not intended to restrict the scope of the appended claims, which themselves recite those details regarded as important to the invention.

What is claimed is:

1. A water purification system for a dental operatory, comprising:
    a mounting bracket suspended from support structure of a dental delivery system;
    mounting structure associated with said mounting bracket, including:
      reservoir support structure,
      germicidal bulb support structure, and
      quartz tube support structure;
    a water reservoir suspended from said reservoir support structure in fluid-tight association therewith;
    a germicidal UV bulb suspended from said germicidal bulb support structure, approximately coaxially with said reservoir, said bulb having a first end proximate said support structure and a second end remote from said support structure;
    a quartz tube held by said quartz tube support structure, approximately coaxially with said germicidal UV bulb;
    an inlet, structured and arranged to deliver water to the interior of said reservoir near said second end of said bulb; and
    an outlet, structured and arranged to receive water from the interior of said reservoir from a location near said first end of said bulb.

2. A water purification system according to claim 1, wherein said quartz tube support structure is constructed and arranged to permit removal of said quartz tube while water lines are connected to said inlet and said outlet.

3. A water purification system according to claim 1, structured and arranged to permit removal of said quartz tube while said UV bulb, bulb support structure and reservoir support structure remain in position as defined by claim 1.

4. A water purification system according to claim 3, further structured and arranged such that said quartz tube may be removed without moving said reservoir in a manner tending to spill water from said reservoir.

5. A water purification system according to claim 4, structured and arranged such that said quartz tube can be removed while said reservoir is full of water.

6. A water purification system according to claim 1, wherein the capacity of said reservoir is selected to assure a germicidally effective dwell time of water within said reservoir while water is being withdrawn from said reservoir at a flow rate required by said dental operatory.

7. A water purification system according to claim 6, wherein the capacity of said reservoir is between approximately 16 and approximately 35 cubic inches.

8. A water purification system according to claim 1, structured and arranged to direct water entering said reservoir to a selected region of the interior of said reservoir, whereby to maximize the exposure of fresh water to UV light.

9. A water purification system according to claim 8, wherein water entering said reservoir is directed to a lower portion of said reservoir.

10. A water purification system according to claim 8, wherein water entering said reservoir is directed to the perimeter of the interior of said reservoir.

11. A water purification system according to claim 1, further including an indicator of the operation status of said bulb, said indicator being positioned for visibility from a wide viewing angle.

12. A water purification system according to claim 11, further including a UV-light-reactive interior surface positioned to enhance the visibility of said indicator.

13. A water purification system according to claim 12, wherein said surface is provided by the interior surface of said reservoir constructed of stainless steel.

14. A water purification system according to claim 1, structured and arranged to permit removal of said bulb without tools and without removing said reservoir or said quartz tube from their respective support structures.

15. A water purification system according to claim 1, further comprising means for heating water within said reservoir to above room temperature.

16. A water purification system according to claim 15, further including control means for maintaining the temperature of water within said reservoir to below a selected temperature above approximately human body temperature.

17. A water purification system according to claim 16, wherein said selected temperature is approximately 105° F.

18. A water purification system according to claim 16, further including limit means constructed and arranged to prevent the temperature of the reservoir from exceeding said selected temperature even though said reservoir contains no water.

19. A water purification system according to claim 18, wherein said selected temperature is approximately 105° F.

20. A water purification system, comprising:
    a mounting bracket configured for clamp-on suspension from support structure of a dental delivery system;
    mounting structure associated with said mounting bracket, including:

reservoir support structure,
germicidal bulb support structure, and
quartz tube support structure;

a water reservoir suspended from said reservoir support structure in fluid-tight association therewith;

a germicidal UV bulb suspended from said germicidal bulb support structure, approximately coaxially with said reservoir, said bulb having a first end proximate said support structure and a second end remote from said support structure;

a quartz tube held by said quartz tube support structure, approximately coaxially with said germicidal UV bulb;

an inlet, structured and arranged to deliver water to the interior of said reservoir near said second end of said bulb; and an outlet, structured and arranged to receive water from the interior of said reservoir from a location near said first end of said bulb.

21. The water purification system of claim 20, constructed and arranged to permit tool-free removal of said germicidal bulb while water lines are connected to said inlet and said outlet, and without removing said reservoir or said quartz tube from their respective support structures.

22. The water purification system of claim 21, further including an indicator of the operation status of said bulb, said indicator being positioned for visibility from a wide viewing angle.

* * * * *